United States Patent [19]
Beritashvili et al.

[11] Patent Number: 5,610,074
[45] Date of Patent: Mar. 11, 1997

[54] CENTRIFUGAL METHOD AND APPARATUS FOR ISOLATING A SUBSTANCE FROM A MIXTURE OF SUBSTANCES IN A SAMPLE LIQUID

[76] Inventors: David R. Beritashvili, 4/1 Dm. Ulyanov str., apt. 33, Moscow, U.S.S.R., 117333; Maxim V. Myakishev, 8/1 Ak. Korolyov str., apt. 183, Moscow, U.S.S.R., 129515; Gennady M. Ershov, 1121 Zelenograd district, apt. 309, Moscow, U.S.S.R., K460; George P. Georgiev, 7 Gubkin str., apt. 42, Moscow, U.S.S.R.; George I. Kapanadze, 19 Frunze str.,, Sukhumi, U.S.S.R., 384900

[21] Appl. No.: 22,047

[22] Filed: Feb. 24, 1993

[51] Int. Cl.⁶ .................. G01N 1/18; C07H 21/02; C12M 1/12; C12N 1/02
[52] U.S. Cl. .............. 436/177; 436/178; 536/25.4; 435/325; 435/261; 435/410; 435/306.1; 435/308.1; 422/72; 210/787; 210/512.1; 935/19; 494/17; 494/29; 494/37
[58] Field of Search .................. 435/4, 5, 6, 29, 435/30, 287, 288, 289, 291, 311, 310, 312, 803, 240.1, 259, 261, 287.2, 288.2, 288.5, 308.1, 306.1; 422/68.1, 70, 72, 99, 101; 494/23, 27, 29, 36, 37, 42, 56, 67, 68, 69, 70, 17; 210/512.1, 656, 657, 198.2, 198.3, 781, 787; 73/863.21; 436/45, 94, 177, 178, 180, 175; 536/25.4; 935/19, 85

[56] References Cited

U.S. PATENT DOCUMENTS

| | | | |
|---|---|---|---|
| 2,834,541 | 9/1956 | Szent-Gyorgi et al. | 233/26 |
| 3,235,173 | 2/1966 | Unger | 233/17 |
| 3,379,370 | 9/1966 | Anderson | 233/26 |
| 3,586,484 | 5/1969 | Anderson | 23/230 |
| 3,722,789 | 1/1972 | Kennedy | 233/26 |
| 3,873,217 | 7/1973 | Anderson et al. | 356/246 |
| 3,901,658 | 7/1974 | Burtis et al. | 23/259 |
| 4,244,916 | 1/1981 | Guigan | 422/72 |
| 4,422,941 | 12/1983 | Vaughan et al. | 210/657 |
| 4,456,581 | 6/1984 | Edelmann et al. | 422/72 |
| 4,463,097 | 7/1984 | Guigan | 436/45 |
| 4,469,793 | 9/1984 | Guigan | 436/45 |
| 4,519,981 | 5/1985 | Guigan | 422/64 |
| 4,663,296 | 5/1987 | Revillet et al. | 436/45 |
| 4,714,590 | 12/1987 | Guigan | 422/102 |
| 4,756,883 | 7/1988 | Romanauskas | 422/72 |
| 4,787,971 | 11/1988 | Donald | 210/198.2 |

(List continued on next page.)

FOREIGN PATENT DOCUMENTS

4603512/13  11/1988  U.S.S.R. .

*Primary Examiner*—William Beisner
*Attorney, Agent, or Firm*—Thomas Fitting

[57] ABSTRACT

A centrifugal rotor effects the isolation, in a sequence of steps, of a substance from a mixture of substances dissolved, suspended or dispersed in a sample liquid. Multiple samples are processed simultaneously by means of a plurality of fractionation cells, each of which contains a series of interconnected, chambered and vented compartments in which individual steps of the fractionation and isolation procedure take place. Specific steps in the preferred embodiments include lysis, sedimentation, aggregation, sorption, rinsing, and desorption. The specific compartment occupied by the sample liquid or one of its fractions at any stage of the process is governed by the speed and direction of rotation of the rotor and by gravitational force. The interconnections, chambers and passages of each compartment are sized and angled to prevent predetermined amounts of sample and reagent liquids from overflowing the compartment. Predetermined amounts of the reagent liquids required to contact the sample in individual steps of the isolation process are simultaneously delivered to specific compartments of every cell by means of a dynamic flow distributor which accepts partially aerosolized injections of said reagents pipetted from a dosator while the centrifugal rotor is rotating. A method of using the rotor to isolate deoxyribonucleic acid is described. The operation of the centrifuge and the dosator can be controlled and coordinated automatically.

25 Claims, 9 Drawing Sheets

U.S. PATENT DOCUMENTS

| | | | |
|---|---|---|---|
| 4,788,154 | 11/1988 | Guigan | 436/180 |
| 4,812,294 | 3/1989 | Combs | 422/72 |
| 4,832,851 | 5/1989 | Bowers et al. | 210/650 |
| 4,900,446 | 2/1990 | Anderson | 210/657 |
| 4,999,304 | 3/1991 | Robertson | 422/72 |
| 5,032,288 | 7/1991 | Columbus et al. | 210/741 |
| 5,039,401 | 8/1991 | Columbus et al. | 210/117 |
| 5,045,047 | 9/1991 | Hutchins et al. | 494/17 |
| 5,061,381 | 10/1991 | Burd | 210/789 |
| 5,077,013 | 12/1991 | Guigan | 422/64 |
| 5,124,041 | 6/1992 | Sheer et al. | 210/641 |
| 5,186,824 | 2/1993 | Anderson et al. | 210/198.2 |

CENTRIFUGAL METHOD AND APPARATUS FOR ISOLATING A SUBSTANCE FROM A MIXTURE OF SUBSTANCES IN A SAMPLE LIQUID

BACKGROUND OF THE INVENTION

1. Field of the Invention

The present invention relates generally to apparatus and methods for automatically isolating preparative quantities of a substance from a mixture of substances in a sample liquid by sequentially fractionating the sample and contacting the fractions with reagent liquids by means of a centrifugal rotor containing at least one fractionation cell and a dynamic flow distributor which, in combination, allow reagent liquids to flow into and sequentially through one or more compartments of the fractionation cell while the rotor is rotating.

2. Description of the Background Art

Many manual methods involving sedimentation, aggregation, phase separation, sorption, rinsing, desorption and other manipulations for isolating a substance from a sample liquid are well known. Although several of these procedures include centrifugation steps, manual interventions such as pipetting, pouring, mixing, shaking, decanting, etc. are typically required between individual steps.

In a preferred embodiment of the present invention, one or more nucleic acids are isolated from a sample liquid. Typically, the sample liquid initially contains a mixture of biological materials such as cells, dissolved proteins, and nucleoprotein complexes. Manual methods for isolating nucleic acids contained in such mixtures typically begin with lysis, protein denaturation or other manipulations to release elements that contain the nucleic acids sought to be isolated. Residual formed elements are then either trapped by filtration or else centrifuged into a pellet. The cleared sample liquid is then typically contacted with a reagent liquid which neutralizes or otherwise conditions the sample liquid and, optionally, conditions the nucleic acids sought to be isolated. Subsequent steps may include contacting the conditioned sample liquid with one or more reagents which further condition the sample liquid. Optionally, the sample liquid, with or without further conditioning, may contact a material such as a gel, resin, membrane, glass or other surface which selectively retains the nucleic acid sought to be isolated, or a derivative thereof, by adsorption or absorption. Other steps include removing substances with which the nucleic acid may be complexed and extracting the nucleic acid from solution or from the adsorptive or absorptive material.

Attempts to automate the aforesaid manual procedures have heretofore relied generally upon robotic means. The AUTOGEN 540, manufactured by Autogen Instruments, Inc., is an example. Another is the GENEPURE 341 manufactured by Applied Biosystems, Inc. Centrifugation is only incidental to the operation of the former and is not involved in the latter.

Columbus, et al. (U.S. Pat. No. 5,032,288) have disclosed a centrifugal method for extracting deoxyribonucleic acid by phase separation. To our knowledge, however, centrifugal means have not been adapted to carry out multi-step chemical procedures for isolating either substances in general or nucleic acids in particular within the confines of a rotor into which reagents are introduced as the rotor rotates. Such means, which lend themselves readily to automation, are likely to be faster, more accurate and reproducible, and less labor-intensive than manual methods. They are likely to be less expensive to manufacture and maintain than robotic means.

In contrast to their limited employment in multi-step chemical preparative procedures, centrifugal rotors for chemical analyses are common. Typically, they have been variously adapted for separating blood plasma from whole blood and for performing chemical analyses on the separated plasma.

Burd (U.S. Pat. No. 5,061,381) describes a centrifugal rotor which separates plasma from whole blood and, by means of a plurality of internal chambers and passages, combines the plasma with one or more reagents and distributes it to a plurality of individual test wells. In the Burd rotor and other disclosed analytical rotors (e.g., U.S. Pat. Nos. 4,756,883, 4,663,296, 4,244,916), and in the instant invention, a capillary limits the flow of liquid between chambers when the rotor is static. Centrifugal force is required to urge liquid through the capillary. Other analytical rotors similarly employ a plurality of chambers to separate plasma into aliquots, treat it, and mix it with reagents (exemplarily, Anderson U.S. Pat. No. 3,586,484). Also conventional is the use of a combination of centrifugal and gravitational force to control the movement of plasma and reagents between chambers. Additionally, the direction of rotation may be exploited for this purpose (e.g., Guigan, U.S. Pat. Nos. 4,463,097 and 4,469,793).

Typically, rotors adapted for analyzing blood plasma include centrifugal means for distributing substantially equal aliquots of a plasma sample to a plurality of test chambers. Unlike the present invention, however, the distributor means is usually loaded while the rotor is static. This limitation can result in uneven distribution of sample aliquots. A variety of venting systems and overflow chambers have been disclosed to deal with this difficulty. See, for example, Burtis, et al., U.S. Pat. No. 3,901,658. Dynamic loading of liquids has been employed in an effort to overcome the problem of uneven distribution. Anderson, et al. U.S. Pat. No. 3,873,217, for example, have disclosed an analytic rotor capable of being dynamically loaded. However, any unevenness of flow during the injection of liquids into dynamic flow distributors has generally resulted in eneven distribution of sample aliquots.

The aim of the invention is to provide easily automated, centrifugal apparatus and methods for the preparative isolation of a substance from a mixture of substances in a sample liquid, in particular, a nucleic acid. Advantages of such apparatus and methods over the current art include better productivity, accuracy and reproducibility than manual methods, lower manufacturing and maintenance costs than robotic systems, and greater flexibility than other centrifugal means now used for preparative purposes or adaptable therefor.

SUMMARY OF THE INVENTION

According to the present invention, a centrifuge for preparatively isolating a substance sought to be isolated from a mixture of substances comprises a centrifugal rotor having a superior region, an inferior region and an axis of rotation disposed parallel to a gravitational force and normal to the plane of rotation of the rotor.

In a preferred embodiment, two (but optionally more than two) dynamic flow distributors are contained, in a nested fashion, axially within the rotor. The flow distributor effects a flow of a liquid from an injection port in the distributor to one or more receptacles in the rotor. Predetermined amounts of reagent liquids are typically injected, as needed, into either flow distributor from a standard dosator by means of an optionally stainless steel injection pipette which is directed into an injection port in the distributor. The pipette can penetrate through the injection port into the distributor during rotation of the rotor because the injection port is annular.

Each flow distributor comprises a superior, annular ring of material and an opposing inferior annular ring, each of which lies generally in a plane orthogonal to the axis of rotation of the rotor. In the current example, an axial, annular portion of the superior ring is reflected superiorly slightly out of the superior ring plane so that an aspect of the inner surface of the superior ring faces axially. The tip of the injection pipette is advantageously aimed at this inner, axial-facing surface. The axial edge of the inferior ring, which is disposed closer to the axis than the axial edge of the superior ring, is superiorly reflected severely out of the inferior ring plane, preferably so that the axial edge of the inferior ring faces abaxially toward the superior ring. Reagent liquids are ejected from the pipet as a spray or aerosol which hits the axial-facing surface of the superior ring and flows centrifugally along it as a smooth film of liquid. Additionally, aerosolized liquid is captured by the abaxially-facing inner surface of the inferior ring and forms a centrifugally migrating film of liquid thereon.

The radially outward region of each flow distributor further comprises, between the superior and inferior rings in the present embodiment, a plurality of generally funnel-shaped chambers each of which tapers at its radially outermost aspect to terminate as a short, radially oriented capillary tube. The chambers, or funnels, are defined in part by a radially outward portion of the superior ring being reflected inferiorly out of the superior ring plane and a corresponding radially outward portion of the inferior ring being reflected superiorly out of the inferior ring plane so that the radially outward edges of the respective rings lie in closely spaced relationship. In another aspect, the funnels are defined by a plurality of dividing walls, or septa, arranged in a regular radial array, each extending from the superior to the inferior ring. When a film of liquid migrating along the inner surfaces of the rings encounters the edges of the septa, it divides evenly among the funnels and is urged by centrifugal force through the capillary tube at the terminus of each funnel.

Conveniently for the preferred embodiment, the exit of each capillary tube is closely apposed to an entry port opening on the axially-facing wall of a receptacle removeably contained in the rotor. In the preferred embodiment, the receptacle is a fractionation cell. The walls of the cell enclose a plurality of interconnected compartments in which fractions of the sample are variously conditioned. In the preferred embodiment, the sample to be fractionated is introduced by pipet or other suitable means into the first compartment through a first entry port. The sample flows thence through a first passage in the first compartment into a first chamber therein. A plurality of fractionation cells, thus loaded, are placed in a radial position in the rotor.

Said first passage of each cell and a first centrifugal surface defined by the centrifugal wall of the first chamber are angled such that appropriately predetermined volumes of liquid in general and sample liquid in particular exit the first compartment during, and only during, rotation of the rotor. During rotation, liquids exiting the first compartment accumulate in a second compartment. The sizes of, and the spatial relationship between, the first and second compartments are chosen such that appropriately predetermined volumes of liquids in general, if in the second compartment, do not return to the first compartment when rotation stops.

Sedimentable materials suspended or dispersed in the sample liquid can optionally be pelleted in the second compartment by means of a second chamber in the cell, which second chamber is located in the second compartment. In cells designed to pellet sedimentable materials, the second chamber is angled so as to trap, irreversibly, the pelleted sample fraction.

When the rotor is rotating, reagent liquids for variously conditioning the sample are conveniently fed from the first, superiorly placed flow distributor into each cell by way of the first entry port, thence through the first compartment and into the second compartment. The second compartment additionally includes a first vent passage in communication with a first vent port for venting air.

A radially inward-facing surface of the second compartment leading to an inferiorly disposed third compartment defines a second centrifugal surface in each cell. When the rotor is static, liquids in the second compartment flow along this second centrifugal surface into the third compartment which comprises a third chamber and a second passage in communication with a second entry port. As sample liquid and reagent liquid flow along the second centrifugal surface, mixing of the respective liquids is completed.

It is to be noted that the third compartment can be reiterated in alternative embodiments of the invention, with the attendant requirement for an additional flow distributor for each iteration.

Advantageously in the present example, a fourth compartment is provided. In this case, said second passage of each cell and a third centrifugal surface defined by the inferiorly disposed, radially inward-facing centrifugal wall of the third chamber are angled such that appropriately predetermined volumes of liquid exit the third compartment during, and only during, rotation of the rotor. The sizes of, and the spatial relationship between, the third and fourth compartments are chosen such that appropriately predetermined volumes of liquid, if in the third compartment, enter only the fourth compartment when the rotor is rotating.

It is convenient to condition sample fractions in the third or fourth compartments by injecting conditioning reagents into the second, inferiorly placed flow distributor. The injected reagent flows via the second entry port radially outward through the second passage and the third chamber into the fourth compartment.

Optionally, sample may be loaded initially into the third compartment.

In the present example of the invention the fourth compartment in each cell comprises a fourth chamber with a means therein for retaining, selectively and releasably in the preferred embodiment, the substance sought to be isolated. The retention means can be, without limitation, a membrane, a gel, a resin, or beads, microspheres, or fibers of glass or other suitable material. The fourth compartment, in the present example, further comprises a means for permitting outflow of liquid from the fourth chamber, in this case a radially oriented capillary passage which provides a predetermined resistance to flow. In the preferred embodiment, liquids exiting the capillary passage under a centrifugal force enter a fifth chamber which serves as an antechamber to a radially outward sixth and seventh chambers. The sixth chamber, which is removeably attached to the cell, is a sample collection chamber. The seventh chamber, which lies in substantially the same plane as the sample collection chamber, is a waste collection chamber. A second vent passage extends from the waste collection chamber to a second vent port.

When the rotor is rotated in a first direction, liquids entering the antechamber are directed by a combination of centrifugal and Coriolis forces into the waste collection chamber. When the rotor is rotated in a second, opposite direction, the Coriolis force vector is reversed and liquids are directed into the sample collection chamber. Only when a liquid entering the antechamber is expected to contain the substance sought to be isolated is the rotor directed in the second direction.

Conventional means, typically controlled by a suitably programmed computer, coordinate the operation of the dosator and the centrifuge to effect the automatic performance of the apparatus.

BRIEF DESCRIPTION OF THE DRAWINGS

The preferred embodiment is taken as an example of the invention with reference to the accompanying drawings, in which.

DETAILED DESCRIPTION

Figure 1:
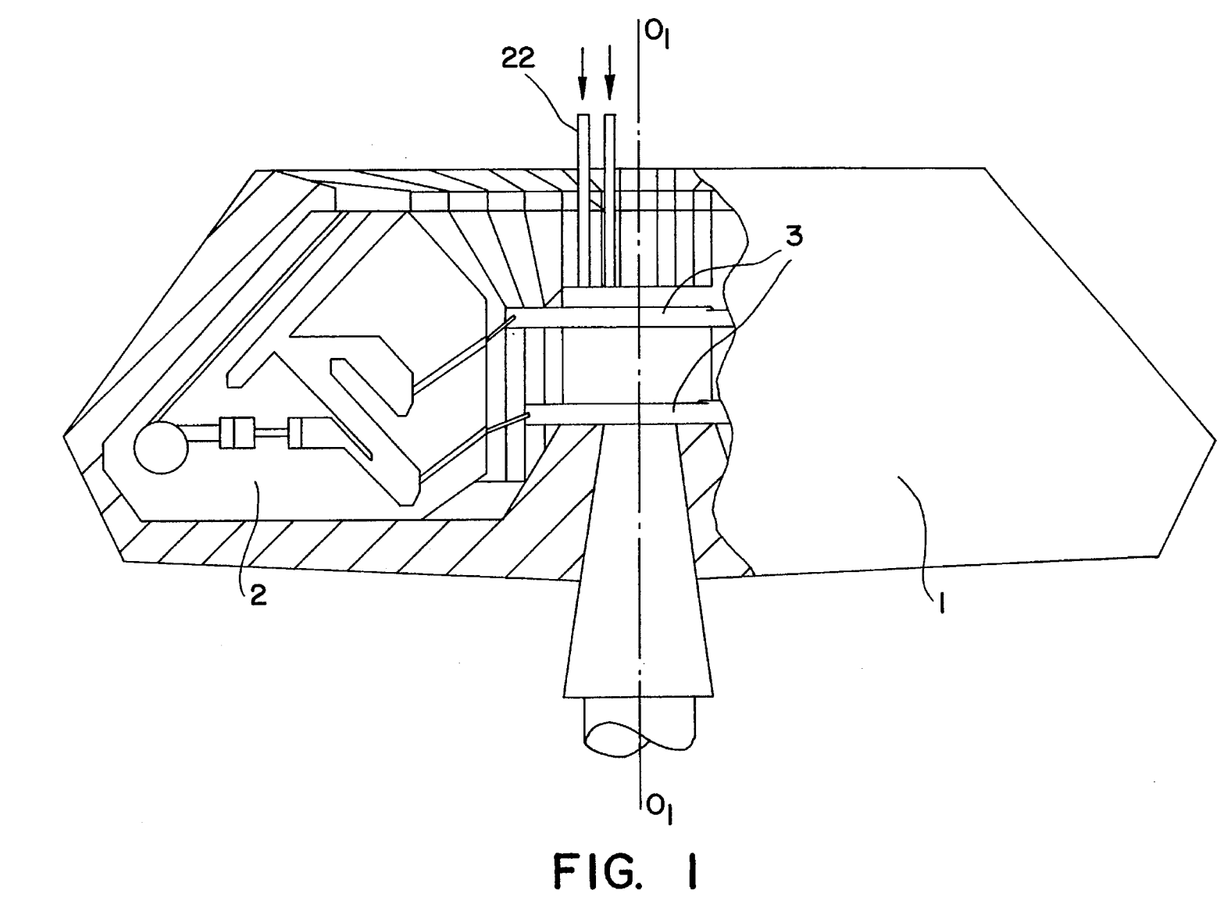
FIG. 1 is a diagrammatic, cut away, partially perspective side view of the apparatus in accordance with the invention.

In FIG. 1, and generally in all the figures, the rotor is designated 1, fractionation cell(s), 2, and the flow distributor(s), 3. The rotor is disposed about an axis of rotation O1—O1. Injection pipettes 22 are partially revealed in FIG. 1. Any of several commercially available multi-channel dosators or automatic pipetting machines may be employed to deliver reagent liquids via the injection pipettes to the flow distributors. In the present example, the rotor, about 30 cm in diameter, accomodates 30 fractionation cells each capable of fractionating a 1 ml sample.

Figure 2:
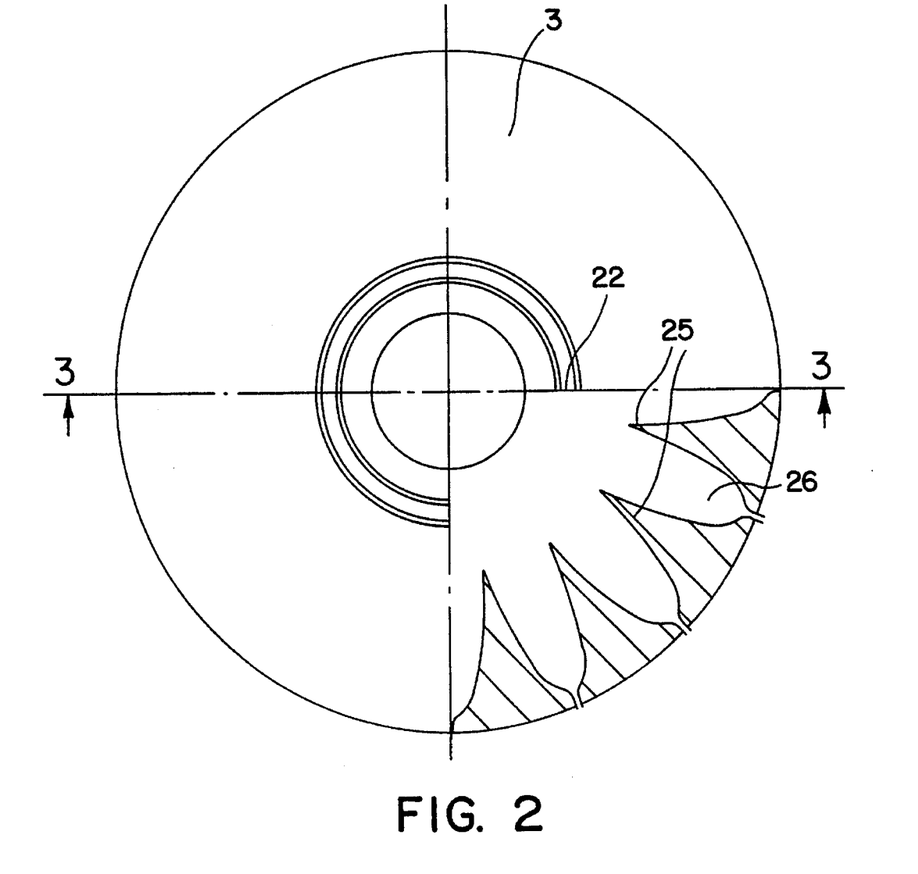
FIG. 2 is a view onto the superior surface of an exemplary dynamic flow distributor, one quarter of which surface is cut away to reveal a horizontal section through the distributor.
Figure 3:
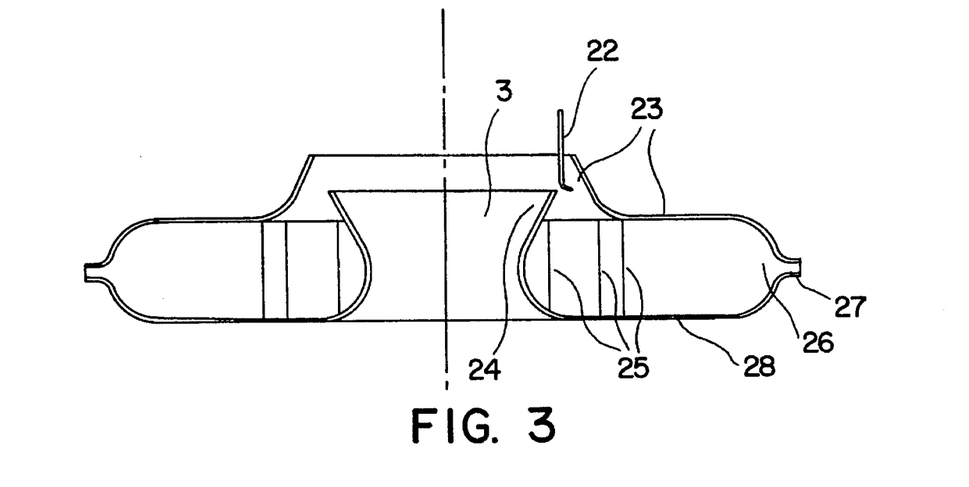
FIG. 3 is a cross-section along line A—A of FIG. 2.

With reference to FIG. 3, it can be seen that the present embodiment of the flow distributor comprises a superior annular ring 23 and an inferior annular ring 28. Each ring generally occupies a plane orthogonal to the axis of rotation. However, the radially outward edge of the superior ring is reflected, first, inferiorly and then in a radially outward direction. Correspondingly, the radially outward edge of the inferior ring is reflected, first, superiorly, and then in a radially outward direction. The respective radially outward edges of the superior and inferior rings are thus closely opposed to define a space sufficient to accomodate a capillary tube 27. Additionally, an axial portion of both the superior and the inferior ring is reflected superiorly. Advantageously, the reflection of the inferior ring is severe enough to create a radially outward concavity 24. There remains between the axial edges of the superior and inferior rings a generally narrow, annular space defining an injection port. The injection port is indicated in FIGS. 2 and 3 by the injection pipette which is shown penetrating therethrough.

Figure 4:
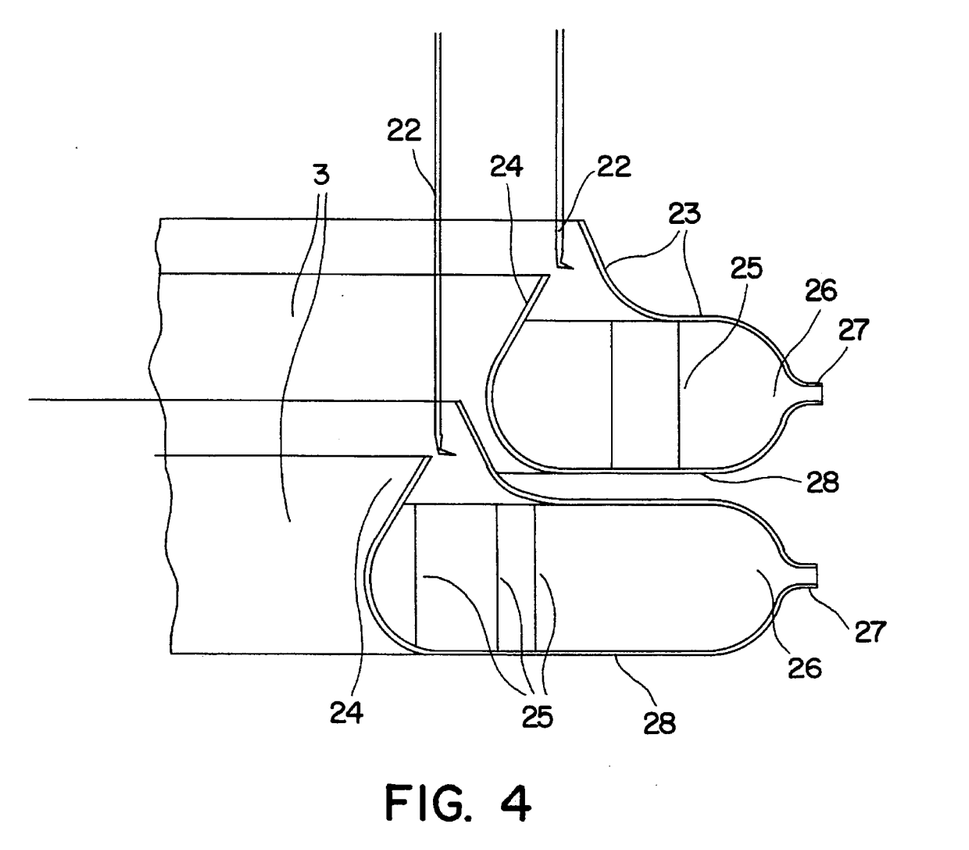
FIG. 4 is a hemi-cross-section of a nested pair of flow distributors showing a first, superiorly placed flow distributor and a second, inferiorly placed flow distributor.

The radially outward region of the flow distributor contains a plurality of funnels 26 defined by the superior and inferior rings and by a plurality of regularly spaced septa 25 (see FIGS. 2 and 3) extending from the superior to the inferior ring. Each funnel merges radially into the capillary tube 27. Two flow distributors, nested as shown in FIG. 4, are appropriately employed in the present example.

Figure 5:
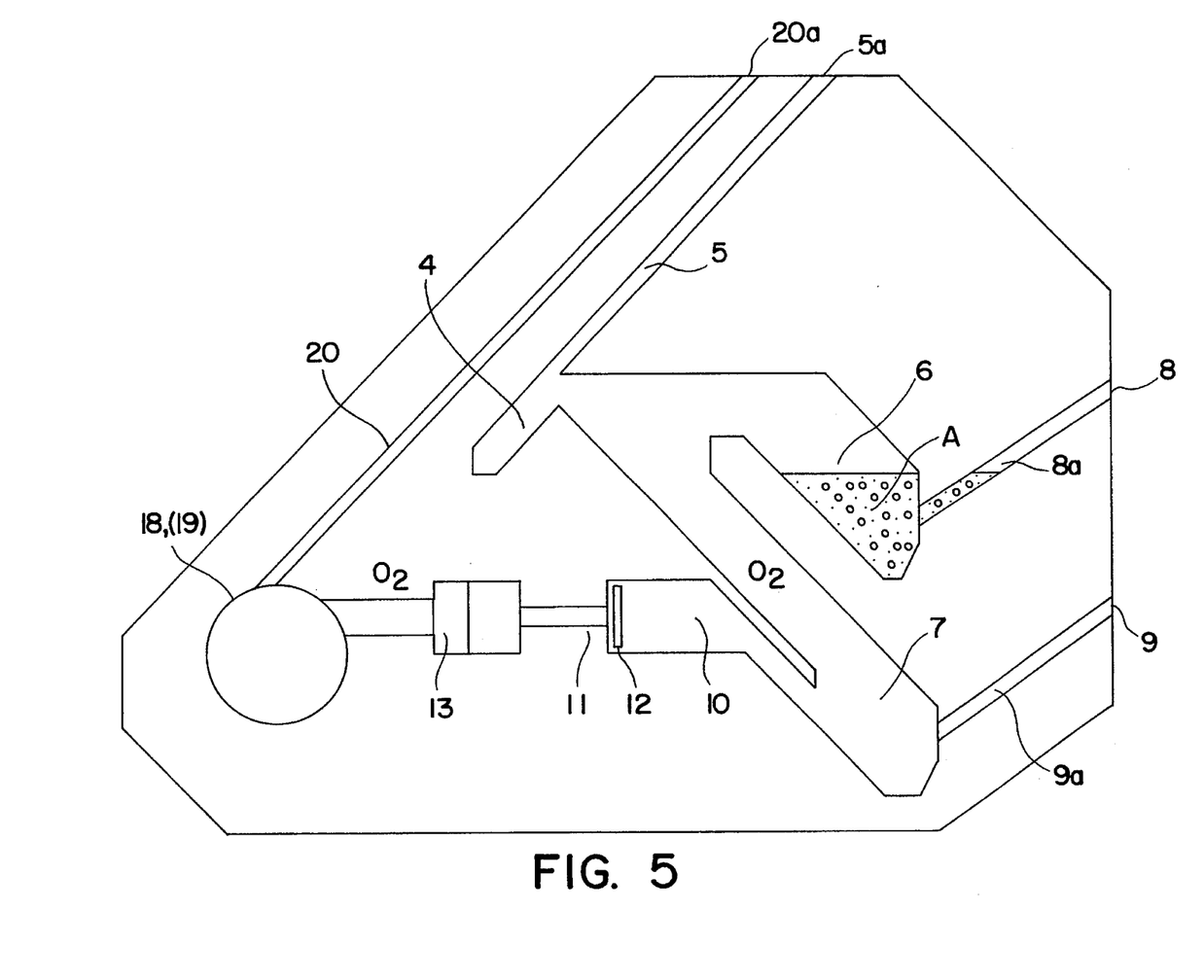
FIG. 5 is a diagrammatic plan view, in longitudinal section, of a fractionation cell loaded with sample liquid.
Figure 5A:
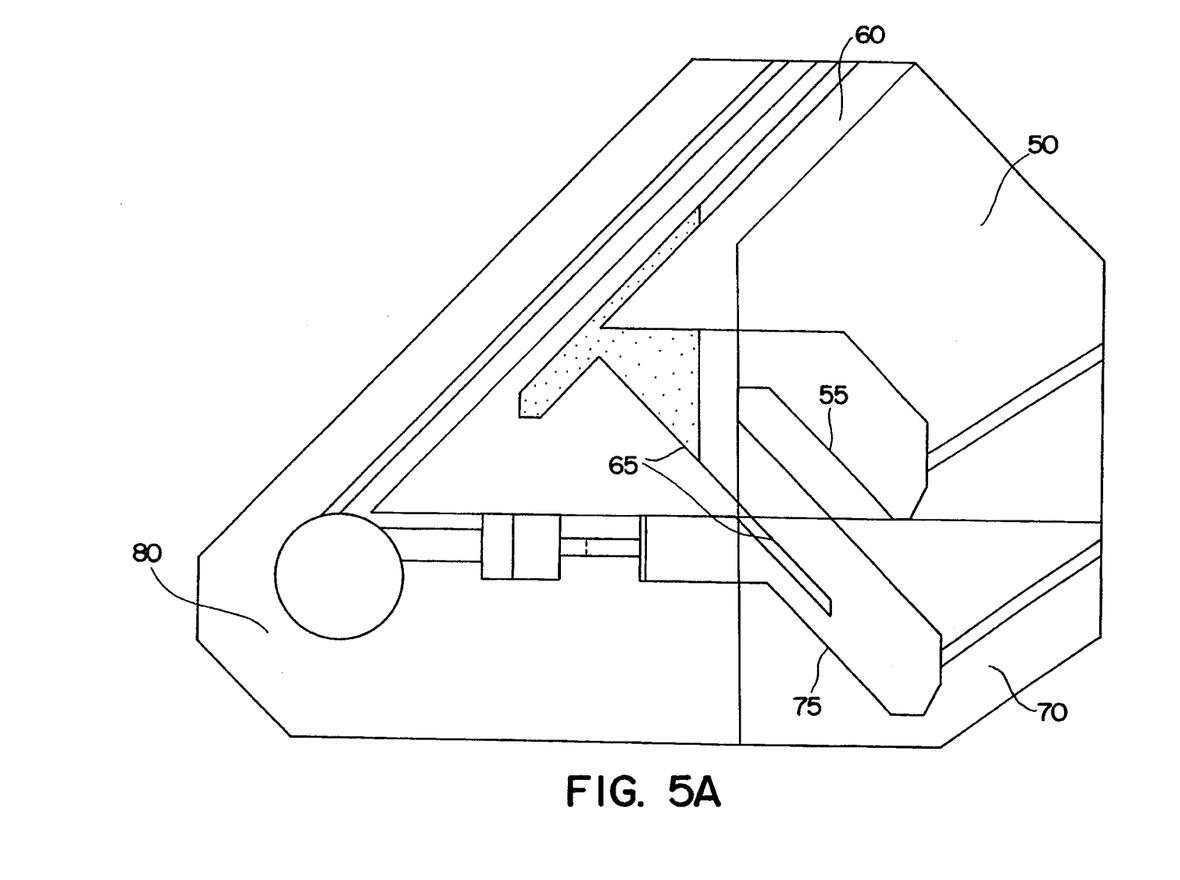
FIG. 5A is the same as FIG. 5, but shows the boundaries of the compartments comprising a fractionation cell.
Figure 6:
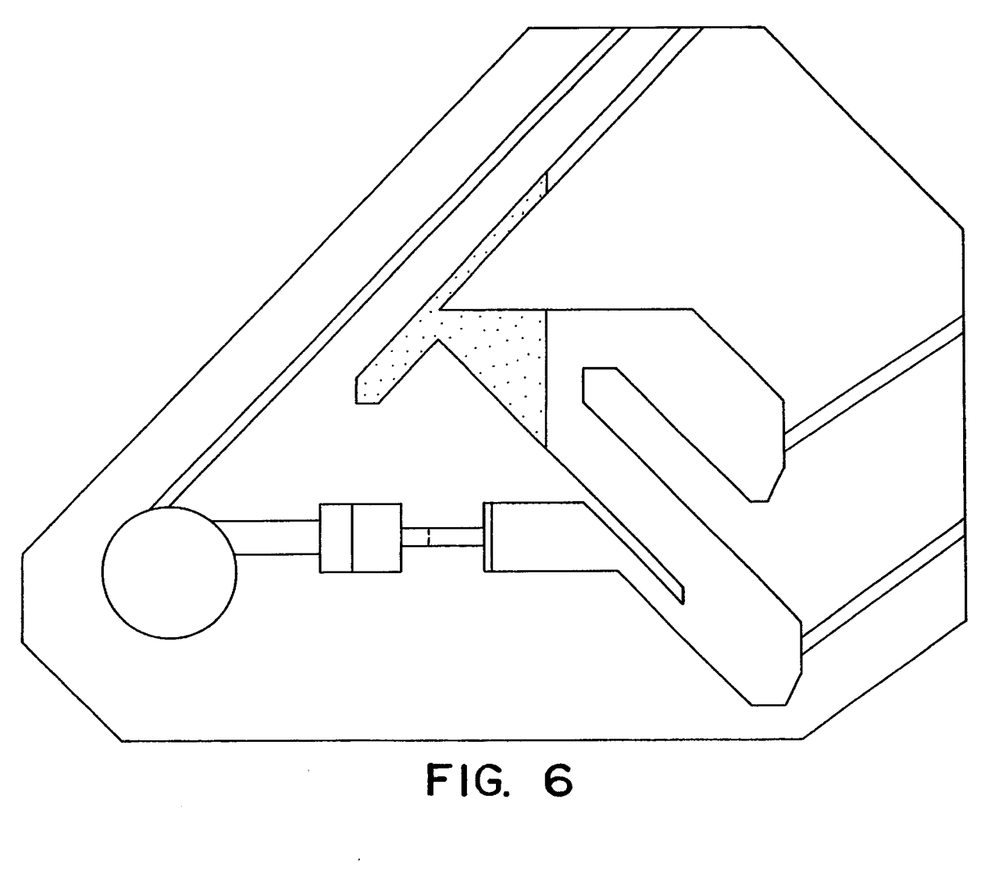
FIGS. 6, 7 and 8, are views similar to FIG. 5, showing successive stages in the use of the apparatus.
Figure 7:
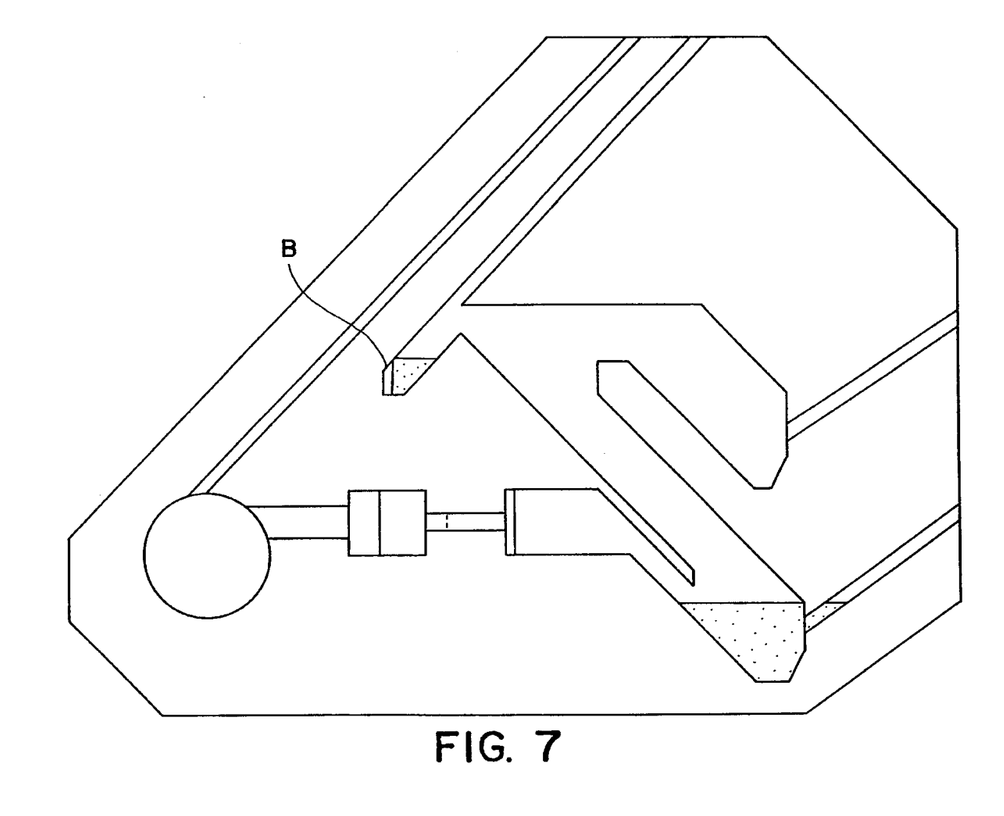
Figure 8:
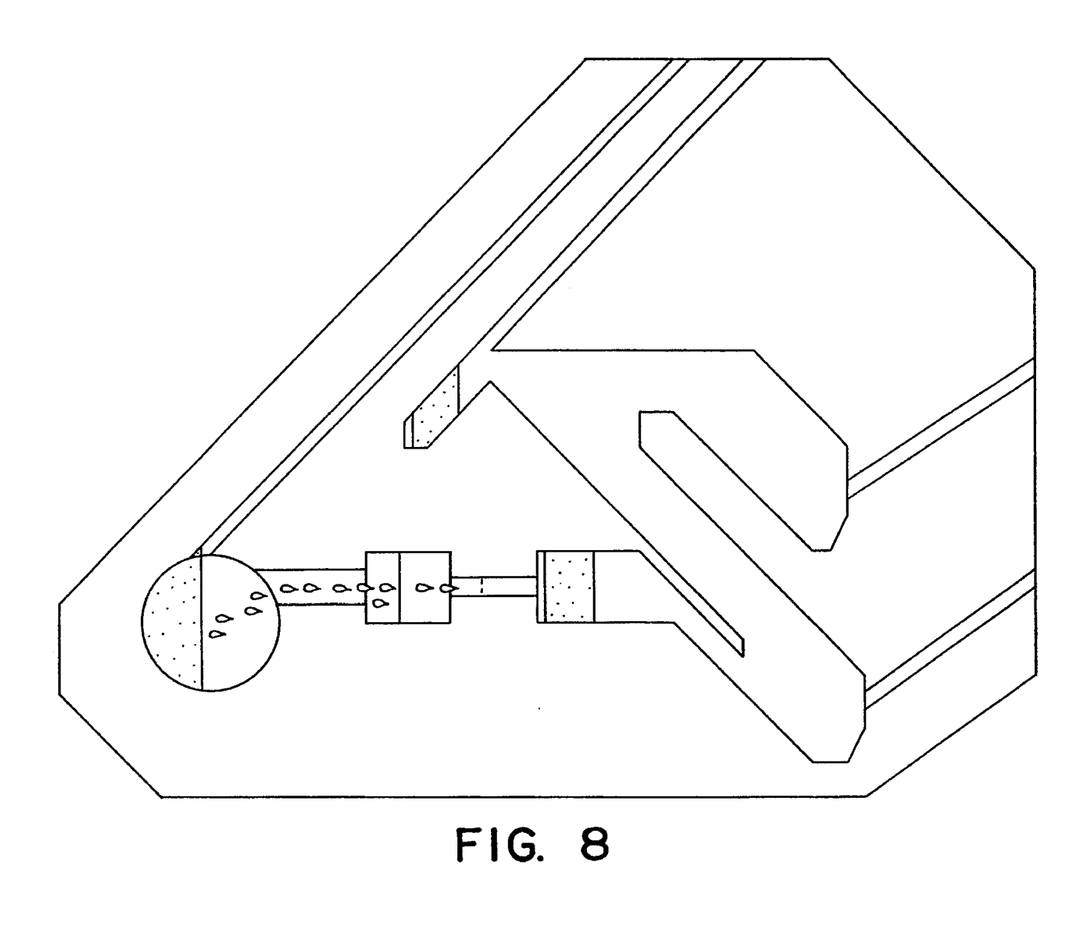

The fractionation cell preferred in the current example is conceptually divided into four compartments in FIG. 5A. Defined by the walls of the fractionation cell, the several compartments contain a plurality of interconnecting passages and chambers schematically represented in FIG. 5. A first compartment 50 comprises a first chamber 6 and a first passage 8a connecting the first chamber to a first entry port 8. The first entry port is aligned in close apposition (See FIG. 1) to the capillary tube extending from a corresponding funnel in the superiorly placed flow distributor (See FIGS. 3 and 4). A second compartment 60, disposed in a generally radially outward direction relative to the first compartment, comprises a second chamber 4, vented via a first vent passage 5 which opens to the outside of the cell at a first vent port 5a. Radially inward from and inferior to the second compartment is a third compartment 70 comprising a third chamber 7 and a second passage 9a connecting the third chamber to a second entry port 9. The second entry port is aligned in close apposition to the capillary tube extending from a corresponding funnel in the inferiorly placed flow distributor (see FIG. 1). Radially outward from the third compartment is a multi-chambered fourth compartment 80 comprising a fourth chamber 10 which contains a retention means 12 for retaining a substance sought to be isolated during the fractionation procedure; an outflow means 11, in this case a capillary passage to provide a predetermined resistance to flow at a given centrifugal force; an antechamber 13; a waste collection chamber 18; and a sample collection chamber 19. The waste collection chamber is vented via a second vent passage 20 which opens to the outside of the cell at a second vent port 20a.

Figure 9:
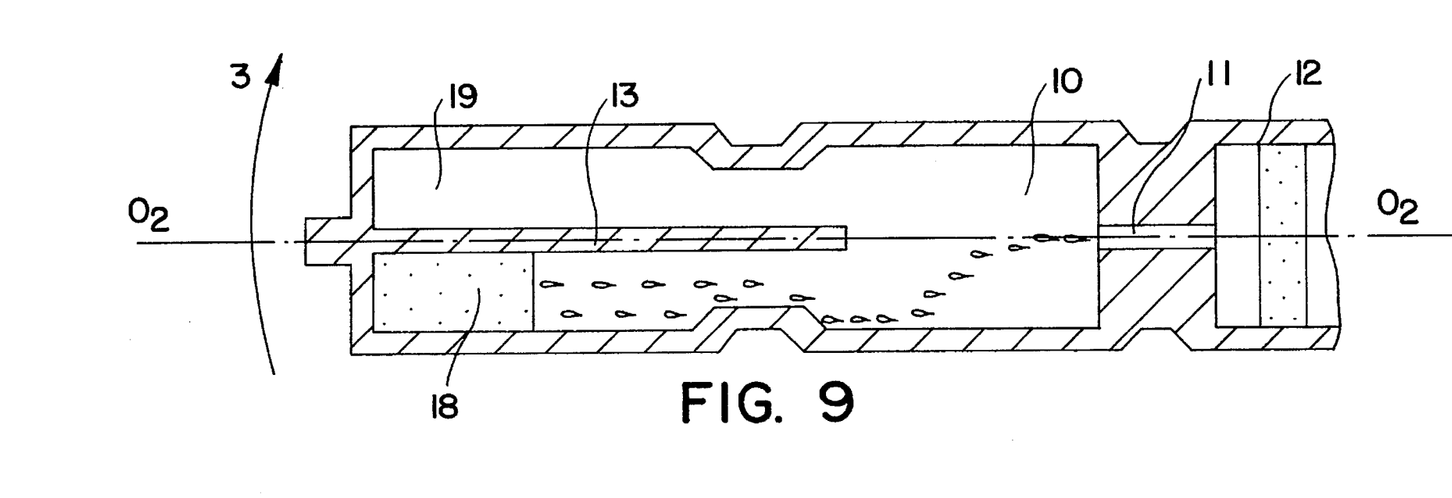
FIG. 9 is a schematic view, in horizontal cross-section, of the fourth compartment of the fractionation cell depicting the waste-collection stage in the use of the apparatus.
Figure 10:
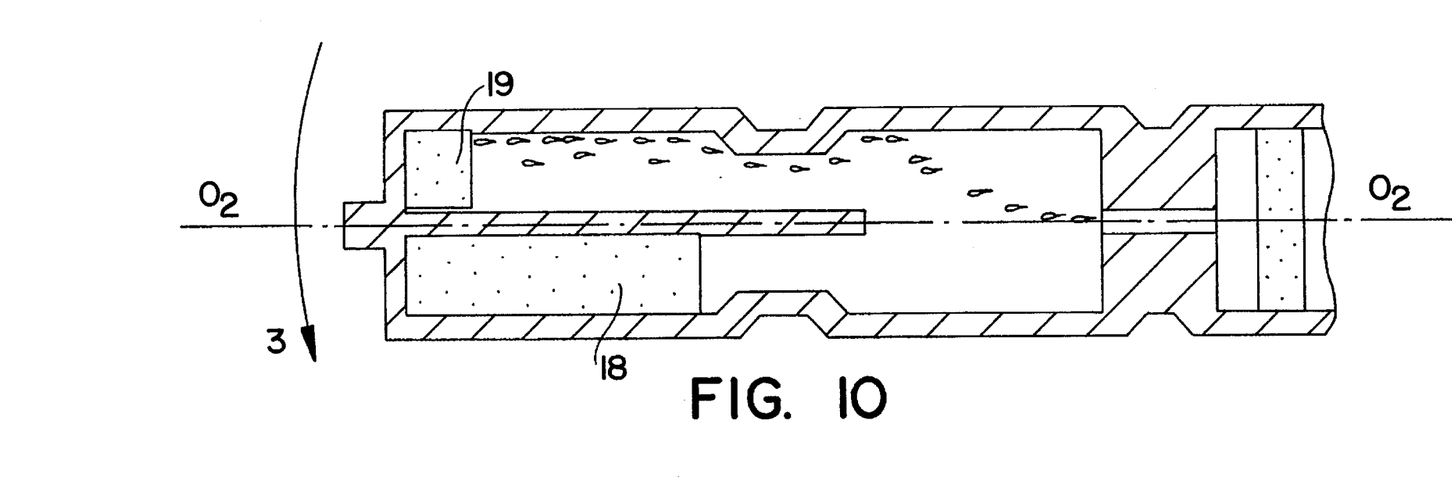
FIG. 10 is a view similar to FIG. 9, showing the sample collection stage in the use of the apparatus.

The aforementioned antechamber, waste collection chamber and sample collection chamber are better viewed and described with reference to FIGS. 9 and 10. The antechamber is in open communication with both the waste collection chamber and the sample collection chamber. The latter two chambers are disposed in generally the same plane of rotation. Advantageously, the sample collection chamber is detachable from the cell.

Referring again to FIG. 5A, note that the first compartment contains, centrifugally, an internal wall extending from a generally radially outward locus superiorly to a radially inward locus inferiorly. Said wall defines, in the first compartment, a first centrifugal surface 55. The second compartment contains a similarly defined second centrifugal surface 65 which is disposed in parallel to the first centrifugal surface and extends out of the second compartment into the third compartment. Disposed in parallel to the second centrifugal surface but generally inferior to it, the third compartment additionally contains a third centrifugal surface 75. These surfaces are advantageous to the operation of the apparatus as will become apparent in the description that follows.

Advantageously, the flow distributors and fractionation cells are made from a suitable plastic material by moulding or stamping. Opposing walls of the cells can be moulded separately and fused together. Similarly, the superior and inferior rings of the flow distributor can be produced separately, brought together in opposition and fused. A rotor to contain the cells and the flow distributors can be readily constructed according to conventional practices to fit commercially available centrifuges. The centrifuge must be capable of impelling the rotor in both directions of rotation and its cover must accomodate the required injection pipettes.

In operation, sample liquid A (see FIG. 5) is loaded into each fractionation cell separately, in this case into the first chamber via the first entry port. The preferable volume of sample liquid exceeds 0.35 ml and, given the size of the cell specified in the current example, should be less than about 2.5 ml. The rotor is rotated in a first direction at a speed and for a time to be determined in part by the sedimentability of materials suspended or dispersed in the sample liquid. The speed must be at least sufficient to result, during this time, in the sample liquid leaving the first compartment along the first centrifugal surface.

To condition the sample in the second compartment with a reagent, a predetermined volume of reagent liquid is injected into the superior flow distributor. In this and other steps, reagent liquid should flow during the injection in a substantially steady stream from the tip of the injection pipette at a rate such that a predetermined volume of reagent liquid is injected over at least about 100 revolutions of the rotor. This is necessary to ensure that the edges of the septa of the flow distributor divide a smooth, thin film of reagent liquid.

Next, the rotor is stopped. Liquid in the second compartment flows along the second centrifugal surface of the cell and accumulates in the third chamber. After a time determined by the nature of the isolation procedure being undertaken, the rotor is rotated again in the first direction. Liquid in the third chamber then migrates along the third centrifugal surface into the fourth chamber where it contacts and passes through the retention means therein. The retention means retains the substance sought to be isolated and, depending upon the nature of the sample, contaminants. While the rotor is rotating, additional reagent liquids may be injected via the inferiorly placed flow distributor to release, selectively, contaminants from the retention means. Liquids flowing through the retention means pass through the outflow-permitting means, in this case a capillary passage sized to cause liquids emerging therefrom to fly into open space as droplets in the antechamber. Coriolis force then directs the droplets to the waste collection chamber. Finally, the rotor is rotated in a second, opposite direction and one or more liquid reagents capable of releasing the substance sought to be isolated are injected into the inferiorly placed flow distributor. When these reagents emerge into the antechamber, Coriolis force directs them into the sample collection chamber.

It will be noted that the substance sought to be isolated can be otherwise conditioned at any stage of the isolation process, including when it is retained on the retention means or after it is collected in the sample collection chamber. The conditioning may be accomplished by contacting the substance with other conditioning reagents, or, exemplarily, by cooling, or by applying heat, radiation, or electrical or magnetic fields.

SPECIFIC EXAMPLES

The following modes of practicing the invention are presented here by way of example and not of limitation.

Isolation of M13 DNA: Manually load 30 samples of an M13 bacteriophage-infected, 6-hour culture of *E. coli*, 1 ml each, into the first chamber of each of 30 four-compartment fractionation cells via the first entry port. Insert the cells into the 30 cm diameter rotor together with two nested flow distributors so that the capillary tubes of the superior and inferior distributors are aligned with the first and second entry ports, respectively, corresponding cells. Insert an injection pipette into each injection port of each distributor and switch on the automatic controller for operating the system.

The controller is programmed for:
(1). Clockwise rotation with a speed of 7000 r.p.m. for 5 minutes: The sample liquid with the suspended *E. coli* flows into the second compartment in each cell under the centrifugal force. An *E. coli* cell pellet is formed in the second chamber. During the last 20 sec. of the centrifugation, sufficient 10% acetic acid is added through the superior distributor to distribute 100 µl of the reagent liquid to each cell.
(2). 2 minutes pause in rotation: Immediately after the rotation stops, substantially all of the sample liquid and reagent liquid flow along the centrifugal surface of the second comparment and mix. The conditioned sample liquid accumulates in the third compartment and the M13 bacteriophage aggregate therein.
(3). Clockwise rotation with a speed of 7,000 r.p.m. for 1 minute: The aggregated phage particles move in the conditioned sample liquid along the third centrifugal surface in each cell into the fourth compartment. The sample liquid flows through a GF/C Whatman filter or equivalent contained therein, thence through an outflow capillary into an antechamber in the form of droplets in flight. The combination of centrifugal force radially and Coriolis force tangentially urges the droplets into the waste collection chamber. The aggregated phage particles remain behind on the glass filter.
(4). Continued clockwise rotation for 3 minutes: Sufficient sodium perchlorate solution is injected into the inferior flow distributor to distribute 1 ml of the solution into each cell. The perchlorate reagent removes phage protein selectively from the filter because DNA does not dissolve in the ionic strength solution.
(5). Continued clockwise rotation for 1 minute: Sufficient 70% ethanol is injected into the inferior flow distributor to distribute 1 ml. of ethanol to each cell. The ethanol removes traces of sodium perchlorate from the filter. Purified DNA is retained.
(6). Reversed (anticlockwise) rotation at 300 r.p.m. for 20 sec.: Inject sufficient low ionic strength buffer (or water) into the inferior distributor to distribute 20 µl to each cell. At this force, the filter absorbs the buffer (or water) without releasing it.
(7). 10 minutes pause: DNA desorbs from the filter into the low ionic strength solution.
(8). Anticlockwise rotation for 20 sec. at 7000 r.p.m.: Centrifugal force urges the DNA solution out of the filter, through the capillary outflow and antechamber and into the sample collection chamber.

The total time for extraction is 20 minutes. The quality and quantity of the M13 DNA obtained by using the above procedure were estimated by agarose electrophoresis (using standard quality markers) as well as by sequencing. The yield from the automated process was the same as that of standard manual (phenolic) procedures at 3–5 micrograms per milliliter of *E. coli* culture, or 50–80% of the total amount.

Extraction of DNA from whole blood: The radially outermost aspect of the second chamber is absent from cells adapted for extracting DNA from whole blood. Otherwise, the procedure is similar to the first example: Load 30 1 ml samples of blood plasma treated with anticoagulant into each of 30 cells, insert cells and distributors in rotor, insert injections pipettes, and activate automatic controller for:

(1). Clockwise rotation for 18 sec: A lysing reagent is added to the blood via the superior flow distributor.

(2). 6 second pause in rotation: Blood and lysing reagent flow into the third compartment. Cells suspended in the blood are lysed during the process.

(3). Clockwise rotation for 2 minutes: Lysate is filtered through the filter in the fourth chamber of the cell. The filtrate, including cellular debris, passes through the GF/C Whatman filter and is discarded in the waste collection chamber while nuclei and nucleoprotein is retained on the filter. sodium perchlorate and ethanol washes follow to remove proteins selectively from the filter.

(4) Anticlockwise rotation for 18 sec. at 300 r.p.m.: An eluting solution (TE buffer with Triton X100) is distributed and is captured on the filter.

(5). 7 minutes pause: DNA desorbs from the filter into the eluting solution.

(6). Anticlockwise rotation for 18 sec. at 7000 r.p.m.: DNA-containing eluant escapes the filter and collects in the sample collection chamber.

The total time for extraction is 10 minutes. The quality and quantity of genomic DNA extracted was assessed by agarose electrophoresis (using standard quality markers) as well as by sequencing. The yield of genomic DNA obtained through the automated procedure is 8–13 micrograms per milliliter of blood, or 50–80% of the total amount, the exact percentage depending upon the freshness of the blood sample.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawings and description in this disclosure are preferred to facilitate comprehension of the invention and should not be construed to limit its scope.

We claim:

1. A method of isolating a substance sought to be isolated from a mixture of substances in a sample liquid comprising the following steps:

(a) loading a first compartment of a fractionation cell with a predetermined volume of the sample liquid by way of an entry port opening into the first compartment;

(b) inserting the cell into a centrifugal rotor equipped with a dynamic flow distributor;

(c) rotating the rotor in a first direction at a first predetermined speed to cause the sample liquid to flow into a second compartment of the cell;

(d) while continuing to rotate the rotor, injecting a predetermined volume of a first liquid reagent into a first flow distributor, said first flow distributor being aligned to permit a flow of the first reagent into the first compartment of the cell and therethrough to the second compartment where the first reagent contacts and mixes with the sample liquid to form a conditioned sample liquid;

(e) stopping rotation of the rotor to permit the conditioned sample liquid to flow away from a material sedimented in a chamber in the second compartment during step (d) and into a third compartment of the cell;

(f) rotating the rotor again in the first direction at the first predetermined speed to cause the conditioned sample liquid to flow into a fourth compartment wherein the conditioned sample liquid contacts a retaining means fixed within the fourth compartment for releasably retaining, selectively, the substance sought to be isolated;

(g) while continuing to rotate the rotor to cause the conditioned sample liquid to pass through the fourth compartment into a waste collection chamber, injecting a predetermined volume of a second reagent into a second flow distributor, said second flow distributor being aligned to permit a flow of the second reagent into the third compartment and, therethrough, into the fourth compartment, to elute substances from the retaining means, which retaining means, when contacted by the second reagent, selectively retains the substance sought to be isolated;

(h) while continuing to rotate the rotor to permit the second reagent to flow out of the fourth compartment into the waste collection chamber, injecting a third reagent into the second flow distributor to rinse traces of the second reagent into the waste collection chamber;

(i) rotating the rotor in a second direction at a second predetermined speed less than the first predetermined speed and injecting a fourth reagent into the second flow distributor to cause the retaining means to release the substance sought to be isolated into the fourth reagent;

(j) rotating the rotor in the second direction at about the first predetermined speed to cause the fourth reagent with the isolated substance contained therein to flow out of the fourth compartment into a sample collection chamber.

2. The method according to claim 1 wherein the substance sought to be isolated is selected from the group comprising ribonucleic acid and deoxyribonucleic acid.

3. The method according to claim 2 wherein the sample liquid comprises a suspension of viral particles.

4. The method according to claim 2 wherein the sample liquid comprises a suspension of bacteria.

5. The method according to claim 2 wherein the sample liquid comprises a suspension of plant cells.

6. The method according to claim 2 wherein the sample liquid comprises a suspension of animal cells.

7. The method according to claim 2 wherein the sample liquid is a physiological fluid containing cells suspended therein.

8. The method of claim 2 wherein the first reagent is an aqueous acidic solution.

9. The method of claim 2 wherein the first reagent is a lysing reagent.

10. The method of claim 2 wherein the second reagent is an aqueous solution of sodium perchlorate.

11. The method of claim 2 wherein the third reagent is an aqueous solution of ethanol wherein the concentration of ethanol is about more than 50%.

12. The method of claim 2 wherein the fourth reagent is an aqueous ionic solution of ionic strength about less than 200 milliequivalents per liter.

13. The method claim 2 wherein the retaining means is glass fibers.

14. The method of claim 2 wherein the retaining means is glass beads.

15. The method of claim 1 wherein the temperature of the rotor is controlled between a temperature of about 0° C. and about 100° C.

16. The method of claim 1 wherein steps (c) through (j) are automatically controlled.

17. The method according to claim 1 wherein the substance sought to be isolated is a biopolymer.

18. An apparatus for isolating a substance sought to be isolated from a mixture of substances in a sample liquid, said apparatus comprising, in combination:

a) a centrifugal rotor having a superior region, an inferior region, an axis of rotation disposed in controllable relation to a gravitational force, and a reversible impelling means for applying a predetermined centrifugal force thereto;

b) a fractionation cell contained in said rotor, said cell comprising walls defining an entry port and a plurality of interconnected chambers and passages, said chambers and passages being sized, angled and disposed relative to one another to provide, in combination with said impelling means, a means for controlling a flow therebetween of a predetermined liquid volume under a centrifugal force and said gravitational force, wherein the centrifugal force is a means for constraining and for advancing the flow and wherein the gravitational force is a means for constraining and for advancing the flow, and wherein said interconnected chambers and passages in the cell are distributed among a plurality of contiguous compartments comprising:

1) a first compartment comprising:
      a first chamber for containing said sample liquid and, axially, a first passage connecting the first chamber with a first entry port, the first passage and the first chamber being sized and angled to prevent said liquid volume from overflowing the first compartment when said rotor is static;
      a first centrifugal surface, said centrifugal surface being angled such that centrifugal force urges said liquid volume out of the first compartment into 2) a second compartment, disposed generally in a radially outward direction relative to the first compartment, comprising:
      a second chamber and, superiorly, a first vent passage connecting the second cheer to a first vent port, the second chamber being sized and the first vent passage being sized and angled to prevent said liquid volume from flowing out of the cell under the centrifugal force;
      a second centrifugal surface disposed in parallel to and radially outward from the first centrifugal surface such that gravitational force urges said liquid volume out of the second compartment into 3) a third compartment disposed inferiorly to the first and second compartments, the third compartment comprising:
      a third chamber and, axially, a second passage connecting the third chamber with a second entry port, the third chamber and second passage being sized and angled to prevent said liquid volume from overflowing said third compartment when said rotor is static;
      a third centrifugal surface angled such that centrifugal force urges substantially all of said liquid volume in the third chamber into 4) a fourth compartment disposed radially outward and superiorly in relation to the third compartment, the fourth compartment comprising a fourth chamber and a means for controllably permitting an outflow of said liquid volume from the fourth chamber, whereby, upon sequential exposure of said rotor to said centrifugal and gravitational forces, said sample liquid is urged through said interconnected chambers and passages thereby isolating a substance present in said sample liquid into said fourth chamber.

19. The apparatus of claim 18 wherein the second chamber is sized and angled to retain substantially all of and substantially only a sedimentable material dispersed in said liquid volume, which material is sedimentable under said predetermined centrifugal force.

20. The apparatus of claim 18 wherein said outflow-permitting means is sized to provide a predetermined resistance to flow of said liquid volume.

21. The apparatus according to claim 18 wherein the outflow-permitting means is a capillary.

22. The apparatus of claim 18 wherein the fourth chamber contains a means of selectively retaining, releasably, the substance sought to be isolated.

23. The apparatus of claim 22 wherein the fourth compartment further comprises:
   an antechamber disposed radially outward from the outflow-permitting means;
   a sample collection chamber disposed radially outward from, and in open communication with, the antechamber;
   a waste collection chamber disposed radially outward from, and in open communication with, the antechamber, the waste collection chamber being disposed in closely spaced relationship to the sample collection chamber and lying in substantially the same plane as the sample collection chamber;
   a second vent passage connecting the waste collection chamber to a second vent port.

24. The apparatus of claim 18 wherein the fractionation cell is removably contained in the rotor.

25. The apparatus of claim 18 wherein the fractionation cell contains a vent port.

* * * * *